United States Patent [19]

Barriere et al.

[11] Patent Number: 5,326,782

[45] Date of Patent: Jul. 5, 1994

[54] SALTS DERIVED FROM 26-(DIALKYLAMINOALKYLSULPHONYL)-PRISTINAMYCIN IIB

[75] Inventors: Jean-Claude Barriere, Bures-sur-Yvette; Jean-Pierre Corbet, Ecully; Jean-Marc Paris, Vaires-sur-Marne; Xavier Radisson, Lyons, all of France

[73] Assignee: Rhone-Poulenc Rorer S.A., France

[21] Appl. No.: 961,925

[22] PCT Filed: Jul. 15, 1991

[86] PCT No.: PCT/FR91/00582

§ 371 Date: Jan. 4, 1993

§ 102(e) Date: Jan. 4, 1993

[87] PCT Pub. No.: WO92/01694

PCT Pub. Date: Feb. 6, 1992

[30] Foreign Application Priority Data

Jul. 16, 1990 [FR] France ............................. 90 09037

[51] Int. Cl.$^5$ ................. A61K 31/42; C07D 498/16
[52] U.S. Cl. ................................ 514/411; 540/453; 540/456
[58] Field of Search ................. 540/455, 456; 514/411

[56] References Cited

U.S. PATENT DOCUMENTS 4,775,753 10/1985 Barriere et al. ............... 540/456
4,866,172 9/1989 Chatterjee et al. ............ 540/456
4,931,557 6/1990 Brennan et al. ............... 540/364

Primary Examiner—Robert T. Bond
Attorney, Agent, or Firm—Morgan & Finnegan

[57] ABSTRACT

Di-p-toluoyl tartrate, di-t-butylacetyl tartrate, di-butyryl tartrate and di-i-valeryl tartrate of (dialkylamino-2 alkyl)sulphonyl-26 pristinamycin II$_B$ having general formula (I) wherein Alk represents a straight or branched alkylene radical and R represents straight or branched alkyl radicals, said radicals having from 1 to 10 carbon atoms.

7 Claims, No Drawings

SALTS DERIVED FROM 26-(DIALKYLAMINOALKYLSULPHONYL)PRISTINAMYCIN IIB

FIELD OF THE INVENTION

The present invention relates to novel salts of 26-[(2-dialkylaminoalkyl)sulphonyl ]pristinamycin $II_B$.

26-[(2-Dialkylaminoalkyl)sulphonyl ]pristinamycin $II_B$ of formula

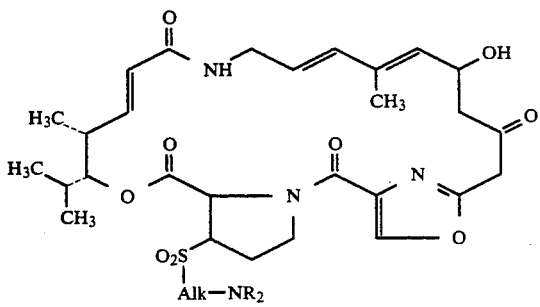

in which Alk represents a linear or branched alkylene radical and R represents linear or branched alkyl radicals, these radicals containing 1 to 10 carbon atoms, are products known for their antibacterial activity and their synergistic action on the antibacterial activity of pristinamycin $I_A$ and its derivatives as has been described in European Patent 191 662.

BACKGROUND OF THE INVENTION

However, the oxidation processes which lead to this sulphone are not always totally satisfactory given that they often lead to an impure product. It is necessary to carry out subsequent purifications, in particular by chromatography, in order to arrive at a product of satisfactory quality.

Moreover, a limited choice of solvents may be used for treating these products. The salts hitherto prepared were soluble in chlorinated solvents or ketones, solvents normally employed for the treatment of pristinamycin $II_B$ sulphones. No acid has allowed until now the preparation of salts which precipitate in the solvents employed.

DESCRIPTION OF THE INVENTION

It has now been found that salts derived from tartaric acid such as di-p-toluoyltartrate, di-t-butylacetyltartrate, dibutyryltartrate and di-i-valeryltartrate of 26-[(2-dialkylaminoalkyl)sulphonyl ]-pristinamycin $II_B$ are salts which are very insoluble in organic solvents and-/or which easily precipitate and as a result make it possible to carry out the purification of this sulphone with very good results.

The salts mentioned above are obtained by salification with the corresponding acid.

The reaction is carried out under the conditions normally used, which do not modify the rest of the molecule. It is carried out in a chlorinated solvent, in particular in methylene chloride, dichloroethane, chloroform, trichloroethylene or tetrachloroethane, or in a ketone, in particular methyl ethyl ketone, at a temperature of between 10° and 25° C.

The salts according to the invention may be reconverted the usual methods in order to release the starting base thus purified.

The novel salts according to the invention are particularly useful by virtue of their insolubility which makes it possible to overcome the purification problems which hitherto existed.

In addition, tartaric acid derived salts of 26-[(2-dialkylaminoalkyl)sulphonyl]pristinamycin $II_B$ furthermore exhibit antibacterial properties and synergistic properties on the antibacterial activity of pristinamycin $I_A$, virginiamycin S and soluble derivatives of pristinamycin $I_A$ and virginiamycin S, previously described in particular in U.S. Pat. Nos. 4,798,827 and 4,618,599.

In vivo, they synergize the antimicrobial activity of pristinamycin $I_A$ in experimental infections of mice with Staphylococcus aureus IP 8203 at a dose of about 75 mg/kg by the oral route (combination 30/70).

Their toxicity is higher than 750 mg/kg by the subcutaneous route.

EXAMPLES

The following examples illustrate the preparation of the products according to the invention.

EXAMPLE 1

A solution of 10.861 g of di-p-toluyltartaric acid (26.05 mmol) in 180 cm$^3$ of dichloromethane is cooled at 15° C. in a 500 cm$^3$ single-necked round-bottomed flask. A solution of 24 g of crude 26-[(2-diethylaminoethyl)-sulphonyl]pristinamycin $II_B$ (26S) (sulphone assay=74.3%) is introduced over 22 minutes into 180 cm$^3$ of dichloromethane while stirring the mixture which becomes cloudy after addition of 60% of this solution and becomes completely clear again at the end of the addition. The mixture of these two solutions is slightly exothermic. 10 minutes after the end of the addition, the salt begins to crystallize. After 3 hours, it is filtered, washed with 3 times 20 cm$^3$ of dichloromethane and dried under reduced pressure.

23.37 g of salt assaying at 100%, or an actual yield of 82.6%, are thus obtained.

The missing di-p-toluyltartaric acid and 26-[(2-diethylaminoethyl ) sulphonyl ]pristinamycin $II_B$ (26S) are wholly contained in the filtrate: this salification is therefore not degradative.

EXAMPLE 2

A solution of 0.21 g of dibutyryltartaric acid (L) (0.7237 mmol) in 0.50 cm$^3$ of methyl ethyl ketone is added dropwise over about 4 minutes and with stirring to a solution of 1.047 g of 26-[(2-diethylaminoethyl)sulphonyl]pristinamycin $II_B$ (26S) assaying at 95.5% (1.4474 mmol) in 5 cm$^3$ of methyl ethyl ketone. The solution remains homogeneous up to the end of the addition. The vessel containing the starting acid is washed 2 times with 0.1 cm$^3$ of methyl ethyl ketone which in turn is added to the mixture. A precipitate is obtained. The mixture is stirred for 2 hours, then filtered on sintered glass (no. 4) and washed with 0.5 cm$^3$ then 2 times with 1 cm$^3$, of methyl ethyl ketone. After drying under reduced pressure (2.7 kPa), 1.1233 g of 26-[(2-diethylaminoethyl)sulphonyl ]pristinamycin $II_B$ dibutyryltartrate (L) is obtained in the form of a white-cream solid melting at 150° C., or a weight yield of 92.8%.

HPLC assay of the salt thus obtained: 97.5%.

EXAMPLE 3

By following the procedure in Example 2, but using 15.6 g of dibutyryltartaric acid (L) in 150 cm³ of methyl ethyl ketone and 75 g of 26-[(2-diethylaminoethyl) sulphonyl]pristinamycin II$_B$ (26S) in 750 cm³ of methyl ethyl ketone, a precipitate is obtained after stirring for 25 minutes. The suspension is placed at 0° C. for 5 hours, then the precipitate is filtered under a nitrogen atmosphere, rinsed with 100 cm³ then 150 cm³ of methyl ethyl ketone then with 3 times 200 cm³ of pentane and then dried under reduced pressure (13.5 kPa) at 30° C. in the presence of phosphorus pentoxide. The white solid obtained (68 g) is then whipped under a nitrogen atmosphere by means of a turbine at 5000 revolutions/-min for 15 minutes in 700 cm³ of pentane and then, after another filtration, for 45 minutes at 6000 revolutions/-rain in 700 cm³ of pentane. The solid is filtered under nitrogen, rinsed with 2 times 100 cm³ of pentane and then dried in the presence of phosphorus pentoxide under reduced pressure (1.35 Pa) at 30° C. 59.9 g of 26-[(2-diethylaminoethyl)sulphonyl]pristinamycin II$_B$ (26S)dibutyryltartrate(L) (88%) are obtained in the form of a white solid, melting at about 150° C. HPLC assay is 97.5%. $[\alpha]_D^{20} = -7.1°(c=0.1, H_2O)$

EXAMPLE 4

A solution of 0.125 g of di-t-butylacetyltartaric acid (L) (0.3619 retool) in 1.25 cm³ of methyl ethyl ketone is added dropwise with stirring to a solution of 0.5747 g of 26-[(2-diethylaminoethyl)sulphonyl]pristinamycin II$_B$ (26S) assaying at 87% (0.7237 retool) in 3.75 cm³ of methyl ethyl ketone. A precipitate is formed immediately following the addition of the first few drops until a thick mass is obtained at the end of the addition. The mixture is stirred for 2 hours, then filtered and washed 3 times with 1 cm³ of methyl ethyl ketone. After drying under reduced pressure (0.13 kPa), 0.5785 g of 26-[(2-diethylaminoethyl)sulphonyl ]pristinamycin II$_B$ (26S) di-t-butylacetyltartrate (L) is obtained in the form of a white precipitate, or a weight yield of 92.64%.

Assay of the salt thus obtained: 96.74%.

EXAMPLE 5

By following the procedure in Example 4 but using 0.38 g of di-t-butylacetyltartaric acid (L) in 5 cm³ of methyl ethyl ketone and 1.5 g of 26-[(2-diethylaminoethyl)sulphonyl]pristinamycin II$_B$ (26S) in 10 cm³ of methyl ethyl ketone, 1.2g of 26-[(2-diethylaminoethyl)-sulphonyl pristinamycin II$_B$ (26S) di-t-butylacetyltartrate (L) (67%) is obtained in the form of a white solid, melting at about 153° C. HPLC assay is 96.8%.

$[\alpha]_D^{20} = -3.4° \pm 0.8°(c=0.51, H_2O)$.

EXAMPLE 6

A solution of 0.23 g of di-i-valeryltartaric acid (L) (0.7237 mmol) in 0.5 cm³ of methyl ethyl ketone is added dropwise with stirring to a solution of 1.047 g of 26-[(2-diethylaminoethyl)sulphonyl]pristinamycin II$_B$ (26S) assaying at 95.5% (1.4474 mmol) in 5 cm³ of methyl ethyl ketone. A precipitate is formed during addition of the solution. The vessel containing the starting acid is washed with 0.2 cm³ of methyl ethyl ketone which is in turn added to the mixture. 1 cm³ of methyl ethyl ketone is added to the now thick mixture. Stirring is pursued for 2 hours, the mixture is filtered on sintered glass (no. 4) and washed with 0.5 cm³ then 3 times 1 cm³ of methyl ethyl ketone. After drying under reduced pressure (0.13 kPa), 1.1245 g of 26-[( 2-diethylaminoethyl)sulphonyl ]pristinamycin II$_B$ (26S) di-i-valeryltartrate (L) is obtained in the form of a white precipitate comprising colored crystals in an amorphous mass, or a weight yield of 91.4%.

Assay of the salt thus obtained: 98.7%.

EXAMPLE 7

A solution of 0.35 g of di-i-valeryltartaric acid (L) in 5 cm³ of in methyl ethyl ketone is added with stirring to a solution 1.5 g of 26-[(2-diethylaminoethyl)sulphonyl]-pristinamycin II$_B$ (26S) in 10 cm³ of methyl ethyl ketone in a 25 cm³ single-necked round-bottomed flask. The precipitate obtained is filtered, washed with 2 times 3 cm³ of methyl ethyl ketone and then with 2 times 20 cm³ of pentane. 1.66 g of a white solid is thus obtained which is recrystallized in 20 cm³ of boiling methyl ethyl ketone. The crystals are filtered, rinsed with 2 times 3 cm³ of methyl ethyl ketone, then with 3 times 20 cm³ of pentane and then dried under reduced pressure (2.7 kPa) at room temperature. 1.23 g of 26-[(2-diethylaminoethyl)sulphonyl]pristinamycin II$_B$ (26S) di-i-valeryltartrate (L) (66%) is thus obtained in the form of a white solid melting at 168°±5° C. HPLC assay is 96.7%.

$[\alpha]_D^{20} = -6.7° \pm 0.9°$ (c=0.5, H$_2$O)

The diacyltartaric acids employed may be prepared according to the method described in European Application EP 007 834 and by Duhamel L. and Plaquevent J. C., Bull. Soc. Chim. France, II, 75–83 (1982).

The salts according to the invention may be used as a purification means as illustrated by the following example:

EXAMPLE OF USE

In this test, all the extraction procedure is carried out 4° C. 2000 g of 26-[( 2-diethylaminoethyl)-sulphonyl]-pristinamycin II$_B$ (26S), di-p-toluyltartrate are added with stirring to a mixture of 38 liters of water and 20 liters of ethyl ether. 500 cm³ of 1N sulphuric acid are added to the suspension over 85 minutes and the mixture is stirred for 20 minutes (pH of about 2). The aqueous phase is decanted and extracted with 3 times 10 liters of ethyl ether and then with 3 times 10 liters of pentane. 500 g of sodium chloride and 10 liters of pentane are added to the aqueous phase and the mixture is stirred for 10 minutes. The aqueous phase is decanted, 10 liters of pentane are added and the mixture is then stirred. A solution of 500 g of potassium bicarbonate in 2500 cm³ of water is added over 70 minutes. The pH of the aqueous phase is 6.8 at the end of the addition. Stirring is pursued for 15 minutes, the aqueous phase is decanted and then extracted with dichloromethane (2 times 2.5 liters). The organic phases are combined, washed with 5 liters of water, then dried over 1.5 kg of magnesium sulphate (1.5 kg) and then filtered over sintered glass. The filter is washed with 2 times 1 liter of dichloromethane. The organic phases are concentrated under reduced pressure (1.35 kPa) at 40° C. to give a yellow syrup. 2 liters of pentane are added to this residue and the mixture is stirred for 10 minutes. 1 liter of solvent is evaporated under reduced pressure (2.7 kPa) at 30° C. and then 4 more liters of pentane are added. The suspension is stirred overnight at 4° C. The solid is filtered on sintered glass no. 3, rinsed with pentane (2 times 2 liters) and dried under reduced pressure (0.067 kPa) at 40° C. for 54 hours to give 1126 g of 26-[(2-diethylaminoethyl)sulphonyl]pristinamycin II$_B$(26S) in the form of a clear yellow powder. HPLC assay is 100%.

The present invention furthermore relates to medicinal products consisting of the salts according to the invention of the product of general formula (I), in the pure state or in the form of a combination with any compatible and pharmaceutically acceptable diluent or adjuvant and/or in combination with pristinamycin I$_A$, virginiamycin S or a soluble derivative of pristinamycin I$_A$ or of virginiamycin S defined in particular in U.S. Pat. Nos. 4,798,827 and 4,618,599. The medicinal products according to the invention may be used by the oral, rectal or topical routes.

By way of compositions for oral administration, tablets, pills, powders or granules may be used. In these compositions, the active product, optionally in the form of a combination, is mixed with one or more inert diluents or adjuvants, such as sucrose, lactose or starch. These compositions may furthermore comprise substances other than diluents, for example a lubricant such as magnesium stearate.

Compositions for rectal administration are suppositories or rectal capsules which contain, in addition to the active product, excipients such as cocoa butter, semisynthetic glycerides or polyethylene glycols.

Compositions for topical administration may be for example creams, pomades, lotions or aerosols.

In human therapy, the novel salt according to the invention is particularly useful in the treatment of infections of bacterial origin. The doses depend on the desired effect and the duration of treatment. For an adult, they are generally of between 2000 and 4000 mg per day.

Generally, the physician will determine the most suitable dose as a function of the age, the weight and any other factors specific to the individual under treatment.

The following example will illustrate a composition according to the invention.

EXAMPLE

Tablets containing 250 mg of active product, having the following composition, are prepared according to the usual technique:

| | |
|---|---|
| 26-[(2-diethylaminoethyl)sulphonyl]pristinamycin II$_B$ (26S) di-p-toluyltartrate (L) | 256.7 mg |
| pristinamycin I$_A$ | 75 mg |
| excipient: starch, hydrated silica, dextrin, gelatine, magnesium stearate: qs | 500 mg |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Salts of 26-((2-dialkylaminoalkyl)sulphonyl) pristinamycin II$_B$ (26S) formula:

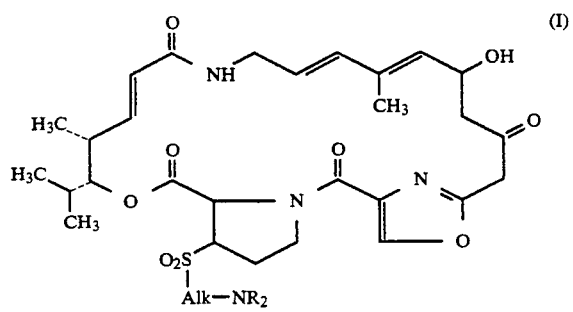

in which Alk represents a linear or branched alkylene radical and R represents linear or branched alkyl radicals, said alkyl radicals containing 1 to 10 carbon atoms, said salts are chosen from di-p-toluyltartrate, di-t-butylacetyltartrate, di-butyryltartrate and di-i-valeryltartrate.

2. [26-[(2-Diethylaminosulphonyl]-pristinamycin II$_B$ (26S) di-p-toluyltartrate]26-((2-Diethylaminoethylsulphonyl)-pristinamycin II$_B$ (26S) di-p-toluyltartrate.

3. [26-[(2-Diethylaminosulphonyl]-pristinamycin II$_B$ (26S) di-t-butylacetyltartrate]26-((2-Diethylaminoethylsulphonyl)-pristinamycin II$_B$ (26S) di-t-butylacetyltartrate.

4. [26-[(2-Diethylaminosulphonyl]-pristinamycin II$_B$ (26S) di-butylryltartrate]26-((2-Diethylaminoethylsulphonyl-pristinamycin II$_B$ (26S) dibutylryltartrate.

5. [26-[(2-Diethylaminosulphonyl]-pristinamycin II$_B$ (26S) di-i-valeryltartrate]26-((2-Diethylaminoethylsulphonyl)-pristinamycin II$_B$ (26S) di-i-valeryltartrate.

6. Pharmaceutical composition comprising a salt according to claim 1, in the form of a combination with any compatible and pharmaceutically acceptable diluent or adjuvant and/or with pristinamycin I$_A$, virginiamycin S or a soluble derivative of pristinamycin I$_A$ or of virginiamycin S.

7. Method for use of a salt according to claim 1 as a purification means for a [26-[(2-dialkylaminoalkyl)sulphonyl]pristinamycin]26-((2-dialkylaminoalkyl)-sulphonyl)pristinamycin II$_B$ as defined in claim 1.

* * * * *

UNITED STATES PATENT AND TRADEMARK OFFICE
CERTIFICATE OF CORRECTION

PATENT NO. : 5,326,782
DATED : 7/5/94
INVENTOR(S) : Barriere, et al

It is certified that error appears in the above-indentified patent and that said Letters Patent is hereby corrected as shown below:

Column 6, lines 30 and 31, delete "[26-[(2-Diethylaminosulphonyl]-pristinamycin II$_B$ (26S) di-p-toluyltartrate]".

Column 6, lines 33 and 34, delete "[26-[(2-Diethylaminosulphonyl]-pristinamycin II$_B$ (26S) di-t-butylacetyltartrate]".

Column 6, lines 37 and 38, delete "[26-[(2-Diethylaminosulphonyl]-pristinamycin II$_B$ (26S di-butylryltartrate]".

Column 6, lines 40 and 41, delete "[26-[(2-Diethylaminosulphonyl]-pristinamycin II$_B$ (26S) di-i-valeryltartrate]".

Colulmn 6, lines 51 and 52, delete "[26-[(2-dialkylaminoalkyl)sulphonyl]pristinamycin]".

Signed and Sealed this

Eleventh Day of April, 1995

Attest:

BRUCE LEHMAN

*Attesting Officer*     *Commissioner of Patents and Trademarks*